United States Patent [19]

Nakanishi et al.

[11] Patent Number: 4,721,647
[45] Date of Patent: Jan. 26, 1988

[54] ABSORBENT ARTICLE

[75] Inventors: Minoru Nakanishi; Akira Sakurai, both of Utsunomiya; Takatoshi Kobayashi, Wakayama, all of Japan

[73] Assignee: Kao Corporation, Tokyo, Japan

[21] Appl. No.: 868,241

[22] Filed: May 29, 1986

[30] Foreign Application Priority Data

May 29, 1985 [JP] Japan ................................ 60-116267

[51] Int. Cl.[4] ............................................. B32B 5/16
[52] U.S. Cl. .................................. 428/283; 427/372.2; 427/385.5; 428/288; 428/327; 428/913
[58] Field of Search ............... 428/913, 327, 283, 288; 427/372.2, 385.5

[56] References Cited

U.S. PATENT DOCUMENTS

| | | | |
|---|---|---|---|
| 4,397,907 | 8/1983 | Rosser et al. | 428/283 |
| 4,460,642 | 7/1984 | Errede et al. | 418/283 |
| 4,481,248 | 11/1984 | Fraige | 428/283 |
| 4,496,623 | 1/1985 | Fraige | 428/283 |
| 4,540,625 | 9/1985 | Sherwood | 428/283 |
| 4,571,359 | 2/1986 | Dutt | 428/283 |
| 4,600,458 | 7/1986 | Kramer et al. | 428/283 |

Primary Examiner—James J. Bell
Attorney, Agent, or Firm—Birch, Stewart, Kolasch & Birch

[57] ABSTRACT

An absorbent article comprises a base material of fibers a part or all of which fibers are hydrophobic and a water-absorbent polymer a part or all of which is in the form of substantially spherical particles and has been bonded to said fibers to surround them. Fixation of the polymer is secured. Softness of the base material is maintained.

10 Claims, 3 Drawing Figures

ABSORBENT ARTICLE

The present invention relates to an absorbent article, and more specifically to an absorbent article in which at least part of a water-absorptive polymer is discontinuously bonded to a fibrous base material while wrapping the base material to thereby prevent the water-absorptive polymer from falling off from the fibrous base material and keep the absorption performance inherent in the water-absorptive polymer without detriment to the hand (pliability) inherent in the fibrous base material even after bonding of the water-absorptive polymer, and which is suitably usable in sanitary and medical articles such as sanitary napkins, disposable diapers, and bandages as well as freshness-keeping materials for vegetables, etc. and water-retaining materials meeting the requirements of absorption and retention of liquid in the fields of agriculture, forestry, civil engineering, etc.

STATEMENT OF PRIOR ARTS

Water-absorptive polymers capable of absorbing water in an amount tens to hundreds of times their own weight have recently been developed and utilized in sanitary articles such as sanitary napkins and paper diapers as well as water retention and water absorption materials in the fields of agriculture, forestry, and civil engineering.

The water-absorptive polymers now in use are generally in granular form. Because of the granular form, they are sandwiched between pieces of paper, contact-bonded in the form of a mixture thereof with pulp by embossing or the like, or heat-sealed with a thermoplastic resin or the like to form composites in most cases of their practical use. Thus, they are used after their form is changed into sheets, films, or the like. However, even according to the method of forming such a composite, falling off of a polymer cannot be avoided. In the case of a heat-sealed composite in which falling off of the polymer is not frequent, since the polymer is coated therearound with a thermoplastic resin, contact of the polymer with a liquid such as water is blocked, disadvantageously resulting in extremely poor water absorption performance.

There have been many proposals for improving these defects to provide an absorbent article which prevents falling off of the polymer, as in the form of a film or a fiber. The absorbent article in film form has poor absorption because of its small surface area, and is limited in pliability because of the presence of the planar polymer. On the other hand, the absorbent article in fiber form is poor in gel strength in the swollen state thereof, though its pliability may be satisfactory. Thus, it is not necessarily true that absorbent articles good in absorption performance and wherein the polymer does not fall off have been obtained.

There has been other proposals involving a method comprising applying a water-soluble monomer capable of being converted into a water-absorptive polymer, such as (meth)acrylic acid or its salt, to a hydrophilic cellulose fiber base material, and subsequently polymerizing the monomer (Japanese Patent Publication No. 500,546/1982 and Japanese Patent Laid-Open No. 204,975/1984). Since the base material is hydrophilic, however, an aqueous solution of the monomer is so liable to penetrate into the inside of the fiber base material that the diameter of the capillaries between the filaments is reduced, leading to poor absorption performance and particularly poor absorption rates. Even when application is made on the surface of the base material without causing penetration therein, the monomer is bonded and polymerized in a wet-spread state over the surface which frequently results in a planar (web-like) form. As a result, when the polymer is swollen with liquid, a blocking membrane is formed on the surface of the fiber to block penetration of the liquid into the inside of the absorbent article, leading to poor absorptivity. Accordingly, an absorbent article having good absorption performance and a polymer which does not fall off has been demanded.

SUMMARY OF THE INVENTION

As a result of intensive investigations with a view to developing an absorbent article excellent in absorptivity and wherein wherein the polymer does not fall off, the inventors of the present invention have found that an absrobent article having a configuration comprising a water-absorbent polymer bonded to a fibrous base material in such a state that at least part of the water-absorbent polymer wraps the fibrous base material in the form of substantial spheres discontinuously bonded to the base material can fully exhibit the absorption performance of the polymer particles and wherein said polymer substantially does not fall off even when swollen. Thus, they have completed the present invention.

An absorbent article according to the invention comprises a base material of fibers a part or all of which fibers are hydrophobic and a water-absorbent polymer a part or all of which is in the form of substantially spherical particles and has been bonded to said fibers to wrap them.

The polymer particles contained in the invention article are fixed onto the hydrophobic fibers to surround the hydrophobic fibers in the cross section. As a result, the fibers appear to insert into the polymer particles. The polymer particles are scattered throughout the base material so as to be discrete and discontinuous from one to another. Moreover they bond to the fibers in the form of spherical or ellipsoidal beads having been tied one to another in a row like a rosary.

In order to work the invention with advantageous effects, preferable features of the invention are introduced below.

The fibers comprise 5 or larger, more preferably 50 or larger, percent by weight of hydrophobic fibers. The hydrophobic fibers consist of filaments having an advancing contact angle against 1 cc of water of 50° to 100°. They are selected from polyester fibers, polypropylene fibers and conjugated fibers of polyethylene and polypropylene.

The invention article can be obtained by a process which comprises the steps of applying an aqueous solution of a water-soluble, ethylenically unsaturated monomer to the base material so that part of the solution drops may wrap and bond to the fibers, polymerizing said monomer to produce the water-absorbent polymer and drying the resulting article.

The invention article is, in other words, defined as an article comprising a fibrous base material and a water-absorptive polymer bonded to said base material, while at least part of said water-absorptive polymer wraps said base material in the form of substantial spheres discontinuously bonded to the base material.

The polymer to use in the invention is water-insoluble.

The absorbent article of the present invention can be obtained according to a method comprising the following steps (1), (2), and (3).

(1) An aqueous solution of a water-soluble, ethylenically unsaturated monomer capable of being converted into an water-absorbent polymer is applied to a fiberous base material containing a hydrophobic fiber therein to obtain a composite having aqueous monomer droplets discontinuously distributed with at least part of the droplets wrapping the fibrous base material.

(2) The monomer in the obtained composite is converted into a water-absorptive polymer in an atmosphere not obstructing polymerization according to a known polymerization method to obtain an aqueous water-absorbent composite.

(3) Subsequently, the obtained water-absorbent composite is dried to obtain a desired absorbent article.

The configuration of the fibrous base material is important in providing such a state that at least part of water-absorptive polymer particles wraps the fibrous base material. Specifically, incorporation of a hydrophobic fiber into a web of the fibrous base material gives such a hydrophobic nature to the fibrous base material that it can provide together with a surface tension a state of wholly wrapping the fiber in the form of substantial spheres (spheres or ellipsoids) when an aqueous monomer solution is applied to the fibrous base material. The fibrous base material capable of providing such a state contains 5 wt. % or more of a hydrophobic fiber of 50° to 100°, preferably 60° to 95° in advancing contact angle of its filaments against water, namely contact angle of them against 1 cc of an ion-exchanged water droplet. Usable hydrophilic fibers include polyester, polypropylene, conjugated polyethylene-polypropylene fibers. Those base materials mainly containing a hydrophobic fiber as mentioned just above are preferred. Instead of such a hydrophobic fiber, a hydrophilic fiber, such as rayon, converted into a hydrophobic one by application to the surface thereof of a sizing agent of, for example, a rosin type or an alkylketene dimer type, a cationic surface active agent, or the like may be used.

An aqueous monomer solution is applied on the fibrous base material having the above-mentioned configuration, and is subjected to polymerization to provide a state wherein polymer particles firmly wrap the fiber. Thus, an absorbent article where the polymer does not substantially fall off even when swollen is obtained. The distribution of the polymer in the form of substantial spheres (spheres or ellipsoids) enlarges the surface area of the polymer per mass. Besides, the absence of a planar continuous polymer allows the absorptivity of the polymer in the absorbent article to be sufficiently exhibited. Thus, a higher absorptivity can be secured all the more. When a hydrophobic fiber having a contact angle of 100° or more against water is used, the water repellency of the fiber is too large, with the result that the polymer particles cannot show a state of wrapping the fiber but merely exist independently on the surface of the fiber or between the filaments though they are formed into spheres. When a fiber having a contact angle of 50° or less is used, the aqueous monomer solution is wet-spread over the fiber so that the purpose of the present invention cannot be attained.

Any water-soluble, ethylenically unsaturated monomer can be used as one to be applied on the fibrous base material having portions of a hydrophobic fiber in so far as it can be converted into a water-absorptive polymer and provide good absorption performance after dried. In general, a water-soluble, ethylenically unsaturated monomer capable of providing such performance has a functional group derived from a carboxylic acid or its salt, phosphoric acid or its salt, or a sulfonic acid or its salt. Specific examples of such a monomer include (meth)acrylic acid and its salts, vinylsulfonic acid and its salts, and vinylphosphonic acid and its salts. (Meth)acrylic acid and its salts are preferred. The polymer to be obtained may be either a homopolymer or copolymer of a monomer(s) as mentioned above or a graft polymer of starch or cellulose with a monomer as mentioned above or the like.

In order to improve the absorption performance, a crosslinking agent or an additive may be added to the monomer. Crosslinking agents that may be used are preferably water-soluble compounds having two or more functional groups capable of reacting with a functional group of a carboxylic, phosphoric, sulfonic acid, or the like, specific examples of which include water-soluble polyfunctional, ethylenically unsaturated monomers such as methylenebisacrylamide, ethylene glycol di(meth)acrylate, and polyethylene glycol di(meth)acrylate; polyglycidyl ethers such as ethylene glycol diglycidyl ether and polyethylene glycol diglycidyl ether; polyols such as glycerin and pentaerythritol; and polyamines such as ethylenediamine.

Examples of additives include finely divided fillers such as talc, clay, and diatomaceous earth.

Any technique may be employed as the method of applying the above-mentioned aqueous monomer solution to the fibrous base material having portions of a hydrophobic fiber in so far as it can provide a manner and amount of application leading to such a state that at least part of the water-absorptive polymer wraps, in the form of discontinuous entity, the fibrous base material. For example, a known printing technique such as a screen or gravure printing technique, an atomizing or spraying technique with a spray, or the like may be employed. In order to increase the efficiency of application, a polymerization-inactive viscosity modifier or a foaming agent may be employed. Pattern printing adapted to the use of the absorbent article may be performed.

The aqueous monomer solution applied to the fibrous base material having portions of the hydrophobic fiber is polymerized according to a known method to be converted into a water-absorptive polymer. Thus, an absorbent article is formed. The polymerization is possible with, for example, heat, light, accelerated electron beams, radiation, ultraviolet rays, or the like. In order to allow the polymerization to proceed rapidly and quantitatively, it is desired to effect the polymerization in a polymerization-inactive atmosphere such as a nitrogen stream. It is necessary to add a water-soluble radical polymerization initiator, in thermal polymerization, or a water-soluble initiator capable of generating radicals with the aid of light or ultraviolet rays, in photopolymerization or ultraviolet polymerization, to the aqueous monomer solution. After polymerization, the resulting aqueous absorbent article may be dried by means of hot air, microwaves, infrared rays, or the like.

In the absorbent article of the present invention, since rigid portions formed by polymer particles are discontinuously distributed on the fibrous base material due to discontinuous bonding of the polymer particles in a state of wrapping the fiber, the production of the absorbent article is effected without detriment to the hand including the pliability which is inherent in the fibrous base material. Thus, it can be favorably utilized in sanitary and medical articles.

The absorbent article of the present invention, which is formed by applying an aqueous solution of an ethylenically unsaturated monomer to a fibrous base material containing at least partially a hydrophobic fiber and polymerizing the monomer, is markedly reduced in falling off of the polymer from the base material since the water-absorptive polymer is discontinuously bonded on ahd around the surface of the fiber of the base material in the form of spherical or ellipsoidal beads while wrapping the fiber without wet-spreading on the fiber of the base material. Since the polymer is not planar but finely spherical, the surface area of the polymer per mass is so large that the absorption capacity and rate of the polymer are considerably improved as compared with those of conventional ones.

The proportion of the polymer bonded in the form of frog's webs and the polymer bonded in the form of beads, and the size of polymer granules can be varied or controlled by varying the proportion of the hydrophilic and hydrophobic fibers in the fiber web of the base material. The absorption performance can be varied depending on the properties required of products. The interpolymer distance, bonding density, and particle size of the polymer can be varied by varying spaces in the fiber web of the base material. Since swelling spaces of the polymer can be varied thereby, the absorption performance of the polymer can be controlled. The amount and position of the polymer applied can be varied pattern-wise when the monomer is applied by printing or the like. This allows the function of the polymer to be more efficient if only the amount of the polymer applied is varied pattern-wise in accordance with respective positions corresponding to a portion where a large amount of liquid is to be retained and other portion in the case of a diaper, a sanitary napkin, etc.

A better hand with a good pliability and without a rough touch can be secured unlike those having a planar polymer, namely a small number of large knots. This is due to a configuration having a large number of small knots which is materialized by the alternate occurrence of rigid portions of the polymer and non-rigid portions of the fiber itself at short intervals. This is possible since spheres of the polymer can be discontinuously bonded in the form of beads. In view of this, when a good hand with a good pliability is necessary, a large amount of a hydrophobic fiber has only to be incorporated, while, when nerve is necessary, a large amount of hydrophilic fiber has only to be incorporated.

The absorption performance required of a product is different depending on the kind of product, e.g., a paper diaper or a sanitary napkin. The absorption capacity of, for example, a diaper can be increased by using a base material containing 90% or more of a hydrophobic fiber. On the other hand, for example, a sanitary napkin, which may have a small liquid absorption capacity, may comprise a base material mainly composed of a hydrophilic fiber represented by rayon. Nerve can be secured by incorporating, for example, 30% or more of a hydrophilic fiber.

A laminate of a hydrophilic fiber web and a hydrophobic fiber web in two layers can also be used. In this case, a gradient of wettability is set between the upper and lower layers of the base material. This can be utilized for facilitating diffusion of liquid or for providing a difference in absorption performance between the upper and lower portions. Thus, the versatility of the absorbent article is broadened. Accordingly, the absorbent article can also be well adapted to any of various purposes by varying the configuration of the base material.

The invention article is unexpectedly improved in respect to feeling of touch to the skin of a user thereof.

BRIEF DESCRIPTION OF THE DRAWINGS

The drawings show electron microscope photographs of the absorbent articles obtained in Example 1.

The following Examples will further illustrate the present invention in detail.

EXAMPLE 1

An aqueous sodium acrylate solution having a solids content of 40wt. % and a degree of neutralization of 70 mol % was prepared. 1 wt. % (based on the sodium acrylate monomer) of sodium persulfate and 500 ppm (based on the sodium acrylate monomer) of methylenebisacrylamide were dissolved in the solution. Thereafter, a nitrogen gas was blown into the solution to remove the dissolved oxygen therefrom. The resulting solution was uniformly sprayed on a hydrophobic fiber web (A) consisting of only a conjugated polyethylene-polypropylene fiber (ES fiber), a fiber web (B) consisting of equal weights of a conjugated polyethylene-polypropylene fiber (ES fiber) and rayon, and a hydrophilic fiber web (C) consisting of only pulp, each having a basis weight of 45 g/m$^2$, with a spray to respectively provide a basis weight of 150 g/m$^2$ (amount of polymer applied: 60 g/m$^2$). The web (C) was used as a control.

Figure 1:
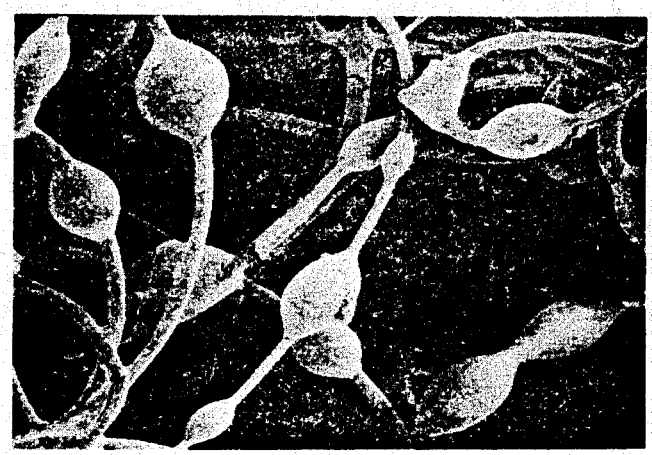
FIGS. 1, 2, and 3 are electron microscope photographs of the absorbent articles obtained by spraying a monomer on the fiber webs (A), (b), and (C), respectively.
Figure 2:
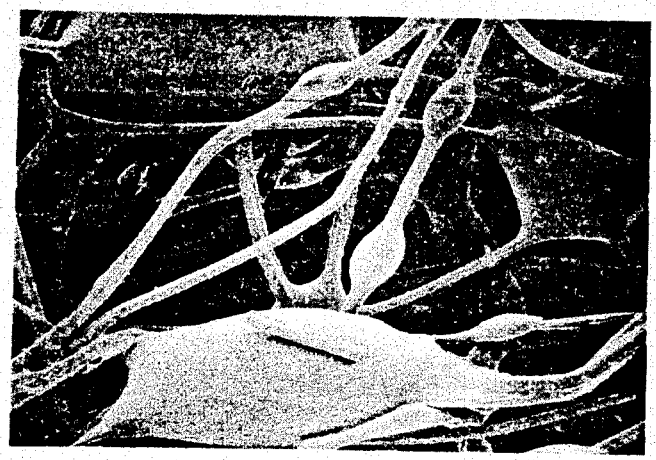
Figure 3:
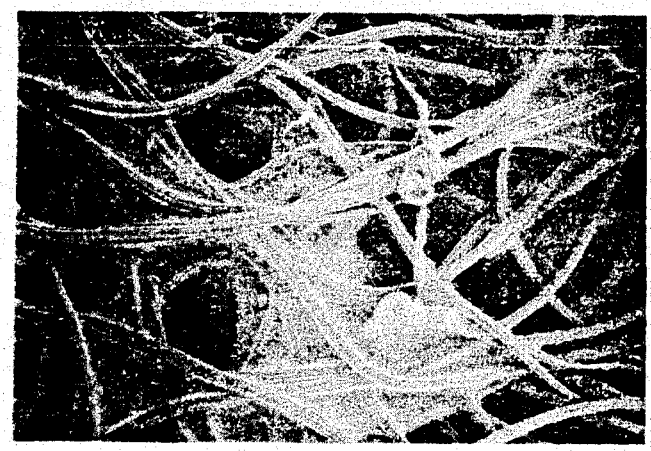

The webs coated with the monomer were allowed to stand in an oven of 70° C. completely purged with nitrogen for 20 minutes to effect polymerization. Thereafter, the resulting composites were dried under reduced pressure at 100° C. to obtain absorbent articles. FIGS. 1 to 3 show electron microscope photographs of the obtained samples. FIGS. 1, 2, and 3 are the electron microscope photographs of the absorbent articles obtained by spraying the monomer on the fiber webs (A), (B), and (C), respectively.

As is apparent from these figures, the web (A) predominantly comprised portions where the polymer was discontinuously bonded in the form of beads to the fiber, while the web (C) mainly comprised portions where the polymer was bonded in a state of being wet-spread like frog's webs. Accordingly, the form of bonding of the polymer can be controlled by controlling the hydrophilic-hydrophobic balance of the fiber of the base material.

These absorbent articles were immersed in a sufficient amount of an isotonic sodium chloride solution, and allowed to stand for 10 minutes. Thereafter, they were allowed to stand on an 80-mesh metallic gauge till dropping of water droplets stopped, and then weighed. The same procedure was repeated as to a base material having the same area as in the above case and no polymer, followed by weighing. The absorption capacity of the polymer was calculated from these weights according to the following formula:

$$\text{absorption capacity (g/g)} = \frac{W_1 - W_0}{W}$$

W: amount of bonded polymer (g)
$W_1$: weight of absorbent article after water absorption (g)
$W_0$: weight of base material after water absorption (g)

The absorption capacities of the obtained absorbent articles are as follows:
one having the fiber web (A): 44 g/g
one having the fiber web (B): 36 g/g
one having the fiber web (C): 20 g/g It can be understood from the above results that the absorption performance can be improved by the presence of the polymer in the form of beads.

Example 2

Polymerization was performed in substantially the same manner as in Example 1 except that an aqueous sodium vinylsulfonate solution having a solids content of 35% and a degree of neutralization of 100%, and 500 ppm of polyethylene glycol diacrylate (trade name: NK Ester A-600 manufactured by Shinnakamura Kagaku K.K.) were used instead of the aqueous sodium acrylate solution and methylenebisacrylamide, respectively.

The absorption capacities of the obtained absorbent articles are as follows:
one having the fiber web (A): 42 g/g
one having the fiber web (B): 35 g/g
one having the fiber web (C): 26 g/g

Example 3

An aqueous potassium acrylate solution having a solids content of 45 wt. % and a degree of neutralization of 70% was prepared. A nitrogen gas was blown into the aqueous monomer solution to remove the dissolved oxygen therefrom. 65 g/m² (amount of polymer applied: 29 g/m²) of the above-mentioned solution was applied on the same fiber webs (A), (B), and (C) as in Example 1 by the screen printing technique.

The resulting coated composites were irradiated with 5 Mrad of electron beams emitted from an EB irradiation apparatus (manufactured by Nisshin High Voltage Company) in a nitrogen atmosphere at 150 kV. Thereafter, they were dried to obtain absorbent articles.

The absorption capacities of the obtained absorbent articles are as follows:
one having the fiber web (A): 30 g/g
one having the fiber web (B): 27 g/g
one having the fiber web (C): 15 g/g

EXAMPLE 4

Polymerization was performed in substantially the same manner as in Example 1 except that an aqueous sodium vinylphosphonate solution having a solids content of 20 wt. % and a degree of neutralization of 100% was used instead of the aqueous sodium acrylate solution.

The absorption capacities of the obtained absorbent articles are as follows:
one having the fiber web (A): 43 g/g
one having the fiber web (B): 34 g/g
one having the fiber web (C): 23 g/g

EXAMPLE 5

Absorbent articles were prepared by varying the polymerization and application conditions as well as the type of base material as listed in Table 1. As to each obtained sample, the form of bonding of the polymer, the absorption capacity, the variation in the head before and after polymerization, and the degree of falling off of the polymer were examined. The results are shown in Table 1.

The form of bonding of the polymer was observed with an electron microscope. The absorption capacity was examined in the same manner as in Example 1. The variation in the hand before and after polymerization was examined by measuring the cantilever value of the base material before and after polymerization (in accordance with JIS L1085 57A) and finding a difference in the value therebetween, which was regarded as a measure of hand loss. More specifically, as the difference was larger, the hand was lost more by bonding of the polymer.

The test for the degree of falling off of the polymer after swelling was conducted by putting a sample into a large amount of an isotonic sodium chloride solution, allowing the polymer to sufficiently swell, stirring them for 5 minutes, and subsequently measuring the weight of polymer fallen off from the base material, followed by. calculation of the weight of the fallen-off polymer according to the following formula:

$$\text{amount of polymer fallen off (wt. \%)} = \frac{\text{weight of polymer fallen off (g)}}{\text{weight of polymer (g)}} \times 100$$

TABLE 1

| Sample No. | Monomer | Crosslinking agent | Application conditions Method | Amount of application (g/m²) | Polymerization method | Base material Hydrophobic fiber (wt %) | Hydrophilic fiber (wt %) | Form | Absorption capacity (g/g) | Difference in cantilever value before and after polymerization (mm) | Amount of polymer fallen off after swelling (wt %) | Remarks |
|---|---|---|---|---|---|---|---|---|---|---|---|---|
| 1 | sodium acrylate | methylene-bisacrylamide | spraying | 65 | thermal polymerization | ES (100) | — | beads | 44 | 4 | 2 | |
| 2 | sodium acrylate | ethylene glycol diglycidyl ether *1 | spraying | 65 | thermal polymerization | ES (100) | — | beads | 43 | 5 | 1 | |
| 3 | sodium acrylate | polyethylene glycol diacrylate *2 | spraying | 65 | thermal polymerization | ES (100) | — | beads | 46 | 2 | 1 | |
| 4 | sodium acrylate | methylene-bisacrylamide | spraying | 65 | thermal polymerization | ES (50) | rayon (50) | beads + frog's webs | 36 | 18 | 5 | |
| 5 | sodium acrylate | methylene-bisacrylamide | spraying | 65 | thermal polymerization | ES (50), PET (50) | — | beads | 46 | 3 | 2 | |
| 6 | sodium acrylate | methylene-bisacrylamide | spraying | 65 | thermal polymerization | — | pulp (100) | frog's webs | 20 | 50 | 15 | comparative |
| 7 | potassium acrylate | — | screen printing | 65 | EB irradiation | ES (100) | — | beads | 42 | 4 | 3 | |
| 8 | potassium acrylate | — | screen printing | 65 | EB irradiation | ES (50) | rayon (50) | beads | 35 | 16 | 7 | |
| 9 | potassium acrylate | — | screen printing | 65 | EB irradiation | — | pulp (100) | frog's webs | 26 | 48 | 14 | comparative |
| 10 | sodium vinylsulfonate | polyethylene glycol diacrylate *2 | spraying | 65 | thermal polymerization | ES (100) | — | beads | 44 | 2 | 3 | |
| 11 | sodium vinylsulfonate | polyethylene glycol diacrylate *2 | spraying | 65 | thermal polymerization | ES (15) | rayon (85) | beads + frog's webs | 34 | 10 | 6 | |
| 12 | sodium vinylsulfonate | polyethylene glycol diacrylate *2 | spraying | 65 | thermal polymerization | — | pulp (100) | frog's webs | 23 | 53 | 18 | comparative |
| 13 | sodium vinylphosphonate | methylene-bisacrylamide | spraying | 65 | thermal polymerization | ES (100) | — | beads | 43 | 6 | 2 | |
| 14 | sodium vinylphosphonate | methylene-bisacrylamide | spraying | 65 | thermal polymerization | ES (50) | rayon (50) | beads + frog's webs | 34 | 18 | 4 | |
| 15 | sodium vinylphosphonate | methylene-bisacrylamide | spraying | 65 | thermal polymerization | — | pulp (100) | frog's webs | 19 | 58 | 13 | comparative |
| 16 | sodium acrylate | methylene-bisacrylamide | gravure printing | 65 | EB irradiation | ES (90), PP (10) | — | beads | 45 | 3 | 1 | |

TABLE 1-continued

| Sample No. | Monomer | Crosslinking agent | Application conditions Method | Amount of application (g/m²) | Polymerization method | Base material Hydrophobic fiber (wt %) | Hydrophilic fiber (wt %) | Form | Absorption capacity (g/g) | Difference in cantilever value before and after polymerization (mm) | Amount of polymer fallen off after swelling (wt %) | Remarks |
|---|---|---|---|---|---|---|---|---|---|---|---|---|
| 17 | sodium acrylate | methylene-bisacrylamide | gravure printing | 65 | EB irradiation | ES (70) | rayon (30) | beads + webs | 38 | 21 | 3 | |
| 18 | sodium acrylate | methylene-bisacrylamide | gravure printing | 65 | EB irradiation | ES (5) | rayon (95) | beads + frog's webs | 30 | 26 | 7 | |

(Note)
*1: trade name, Denakol EX810 manufactured by Nagase & Co., Ltd.
*2: trade name, NK Ester A-600 manufactured by Shinnakamura Kagaku K. K.
In the table, PP is polypropylene fibers, ES is conjugated fibers of polyethylene and polypropylene, and PET is polyethylene terephthalate.

The embodiments of the invention in which an exclusive property or privilege is claimed are defined as follows:

1. An absorbent article comprising a base material of fibers wherein an effective amount of said fibers are hydrophobic, and a water-absorbent polymer, wherein an effective amount of said water absorbent polymer is in the form of substantially spherical particles wherein said spherical particles wrap around and bond to said fibers.

2. An absorbent article as claimed in claim 1 wherein said fibers comprise 5 or more percent by weight of the hydrophobic fibers.

3. An absorbent article as claimed in claim 1, wherein said fiberss comprise 50 or more percent by weight of hydrophobic fibers.

4. An absorbent article as claimed in claim 1, in which said hydrophobic fibers consist of filaments having an advancing contact angle of 50° to 100° against 1 cc of water.

5. An absorbent article as claimed in claim 1, in which said hydrophobic fibers are selected from polyester fibers, polypropylene fibers and conjugated fibers of polyethylene and polypropylene.

6. An absorbent article as claimed in claim 1, in which said hydrophobic fibers consist of hydrohilic fibers which have been treated on the surface to become hydrophobic.

7. An absorbent article as claimed in claim 1, in which said water-absorbent polymer has been bonded to said fibers in the form of spherical or ellipsoidal beads having been tied one to another in a row like a rosary.

8. An absorbent article as claimed in claim 1, in which said base material comprises a layer of hydrophilic fibers and a layer of hydrophobic fibers.

9. An absorbent article as claimed in claim 1, which is obtained by a process comprising the steps of applying in the form of drops an aqueous solution of a water-soluble, ethylenically unsaturated monomer to a base material so that an effective amount of the solution drops may wrap and bond to the fibers, polymerizing said monomer to produce the water-absorbent polymer, and drying the resultant article.

10. A process as claimed in claim 9, in which said monomer is selected from acrylic acid, methacrylic acid, vinylsulfonic acid, vinylphosphonic acid and a salt thereof.

* * * * *